US008895083B2

(12) United States Patent
Solomon et al.

(10) Patent No.: US 8,895,083 B2
(45) Date of Patent: Nov. 25, 2014

(54) COMPOSITION FOR THE MAINTENANCE OF BLOOD SUGAR LEVELS COMPRISING CINNAMON AND GINSENG

(75) Inventors: David Solomon, Toronto (CA); Hector J. Gomez, Jupiter, FL (US)

(73) Assignee: Allegiance Equity Corporation, Toronto (CA)

( * ) Notice: Subject to any disclaimer, the term of this patent is extended or adjusted under 35 U.S.C. 154(b) by 472 days.

(21) Appl. No.: 13/126,097

(22) PCT Filed: Oct. 23, 2009

(86) PCT No.: PCT/CA2009/001528
§ 371 (c)(1),
(2), (4) Date: Apr. 26, 2011

(87) PCT Pub. No.: WO2010/048705
PCT Pub. Date: May 6, 2010

(65) Prior Publication Data
US 2011/0212191 A1 Sep. 1, 2011

(30) Foreign Application Priority Data

Oct. 28, 2008 (CA) .................................. 2642184
May 29, 2009 (CA) .................................. 2667831

(51) Int. Cl.
*A61K 36/258* (2006.01)
*A61K 36/54* (2006.01)

(52) U.S. Cl.
CPC .............. *A61K 36/258* (2013.01); *A61K 36/54* (2013.01)
USPC .......................................... 424/728; 424/739

(58) Field of Classification Search
None
See application file for complete search history.

(56) References Cited

U.S. PATENT DOCUMENTS

2006/0251736 A1* 11/2006 Hayes et al. .................. 424/682
2007/0202215 A1* 8/2007 Lak .................................. 426/61

FOREIGN PATENT DOCUMENTS

| WO | 0162086 A1 | 8/2001 |
| WO | 2007098240 A2 | 8/2007 |
| WO | 2008054695 A2 | 5/2008 |
| WO | WO 2008054695 A2 * | 5/2008 |

OTHER PUBLICATIONS

Mang et al., "Effects of a cinnamon extract on pkasma glucose, HbA and serunm lipids in diabetes mellitus type 2", European journal of Clinical Investigation (2006) 36, 340-344.*
ITMI2008A000219, Ginseng Flavoured Food Composition (Bossi), May 13, 2008.
Mang, et al., Effects of a cinnamon extract on plasma glucose . . . , European Journal of Clinical Investigation, 2006, vol. 36, pp. 340-344.
International Search Report for PCT/CA2009/001528.
Khan et al., Cinnamon Improves glucose and Lipids of People with type 2 Diabetes, Diabetes Care, vol. 26, No. 12, Dec. 2003.
UC Santa Barbara Scientists Discover Cinnamon Compounds' Potential Ability to Prevent Alzheimer's, Journal of Alzheimer's Disease, May 22, 2013.
Cinnamon Compounds Could Help Protect Against Alzheimer's Study Finds, Huffpost healthy Living, Posted May 27, 2013.
Learning About type 2 Diabetes, Alzheimer's Disease and Cinnamon Diabetes Daily Post, Jul. 16, 2013.
Cinnamon the Magic Spice Increases Cognitive Activity, Aug. 7, 2009.
Diabete connection to Alzheimer: a new Discovery, Feb. 18, 2009.
Solomon, TP, Changes in glucose tolerance and insulin sensitivity following 2 weeks of daily cinnamon ingestion in healthy humans, Eur J Appl Physiol. Apr. 2009.
Anat Frydman-Maron, et al., Orally Administrated Cinnamon Extract Reduces B-Amyloid Oligomerizationand Corrects cognitive Impairment in Alzheimer's Disease Animal Models, PLoS ONE 6(1), Jan. 2011, vol. 6, Issue 1.
Alzheimer's Type 3 Diabetes Whole Health Insider dated May 1, 2013.
Bolin Qin, et al, Cinnamon: Potential Role in the Prevention of Insulin Resistance, Metabolic Syndrome, and Type 2 Diabetes, Journal of Diabetes Science and Technology, vol. 4, Issue 3, 685-693, May 2010.

* cited by examiner

*Primary Examiner* — Chris R Tate
*Assistant Examiner* — Deborah Davis
(74) *Attorney, Agent, or Firm* — Caesar, Rivise, Bernstein, Cohen & Pokotilow, Ltd.

(57) ABSTRACT

A composition is disclosed which comprises cinnamon or cinnamon extract such as cinnamon aqueous extract TC 112 and *panax ginseng* or extract from *panax ginseng* standardized to 1.5 to 7% ginsenosides and may comprise an artificial sweetener. The composition is embodied in the form of a pill or food product with 120 mg of cinnamon aqueous extract and 120 mg of ginseng standardized to 1.5 to 7% ginsenosides. The composition is used as a daily dosage for improvement of cognitive function, prevention or treatment of Alzheimer's disease, maintenance or lowering of blood-sugar levels, prevention of arterial disease or the improvement of cognitive function in diabetics.

20 Claims, No Drawings

COMPOSITION FOR THE MAINTENANCE OF BLOOD SUGAR LEVELS COMPRISING CINNAMON AND GINSENG

FIELD OF INVENTION

The present application relates generally to nutritional and medicinal supplements. More particularly, the present invention relates to a composition containing effective amounts of cinnamon for example ginseng extract and cinnamon for example cinnamon extract or their equivalents of polyphenols found in cinnamon and ginosenosides found in ginseng.

BACKGROUND OF INVENTION

Those who have diabetes generally have difficulty in maintaining proper blood sugar levels. Many foods and products are made available to the general public and provide general nutritional health but often are not directed to persons afflicted with diabetes and other glucose/sugar intolerances.

Diabetics may also be prone to other conditions such as coronary artery diseases, dementia, and Alzheimer's disease which may affect memory, cognitive function, and mental health.

The use of ginseng or ginseng extract has been documented as a supplement for use with diabetic patents. However, the use of ginseng in such applications generally requires a relatively large dosage, for example at least 200 mg of standardized ginseng extract.

It would be advantageous to provide a composition which address at least some of the above-noted difficulties.

SUMMARY OF INVENTION

The present application generally provides a composition comprising cinnamon having polyphenols in an effective amount preferably a cinnamon extract and ginseng having an effective amount of genosides preferably a ginseng extract. Thus, the composition may comprise a mixture of polyphenols found in cinnamon and ginsenosides found in ginseng, each in effective amounts.

In another aspect, the present application provides for a use of such a composition to improve cognitive function in diabetics.

In another aspect, the present application provides for a food product containing the composition.

In another aspect of the invention, the composition may be combined with various ingredients such as coca, chocolate, dairy food products, artificial sweeteners (good for diabetics), vitamins and supplements, for example comprising thiamine of B1, Riboflavin, calcium and Niacin.

For example, according to other aspects of the invention, a package of ingredients is provided each package containing an artificial sweetener and at least one ingestible ingredient in an effective non-toxic amount which reduces the impact of blood sugar levels in the body, on the body when the contents of the package are ingested.

According to another aspect of the invention, bulk mix is provided containing an artificial sweetener and at least one ingestible ingredient in an effective non-toxic amount which reduces the impact of blood sugar levels in the body, on the body when ingested.

According to another aspect of the invention, a package (packet or sachet) is provided containing an artificial sweetener and at least one ingestible beneficial ingredient for reducing the impact of blood sugar levels in the body, on the human body.

According to another aspect of the invention, a bulk mix is provided containing an artificial sweetener and at least one ingestible beneficial ingredient in an effective non-toxic amount for reducing the impact of the undesired effect of the ingestion of the table sugar on the human body.

According to another aspect of the invention, the package may be such wherein the at least one beneficial ingredient is selected from an effective amount of cinnamon (or polyphenols found therein), an effective amount of ginseng (or ginsenosides found therein) or combinations thereof.

According to another aspect of the invention, the mix may be such wherein the at least one beneficial ingredient is selected from an effective amount of cinnamon (or polyphenols found therein), an effective amount of ginseng (or ginsenosides found therein) or combinations thereof.

According to another aspect of the invention, a packet is provided containing an artificial sweetener and at least one ingestible ingredient in an effective non-toxic amount which reduces the impact of the blood sugar levels in the body on the body when the contents of the package are ingested wherein the at least one ingestible ingredient comprises at least two ingestible ingredients (in effective non-toxic amounts) which reduce the impact of the blood sugar levels in the body on the body when the contents of the package are ingested.

According to another aspect of the invention, a mix is provided containing a first ingestible ingredient having an artificial sweetener and at least one ingestible ingredient in an effective non-toxic amount which reduces the impact of blood sugar levels in the body, on the body wherein the at least one ingestible ingredient comprises at least two ingestible ingredients (in effective non-toxic amounts) which reduce the impact of the blood sugar levels in the body, on the body when ingested.

According to another aspect of the invention, a paper package is provided containing an artificial sweetener and at least one ingestible ingredient selected from an effective amount of cinnamon (or polyphenols found in cinnamon), ginseng (or ginsenosides found in ginseng, and combinations thereof, for reducing the impact of blood sugar levels in the body on the human body when all are ingested.

According to another aspect of the invention, a bulk mix is provided containing an artificial sweetener and at least one ingestible ingredient selected from an effective amount of cinnamon (or polyphenols found in cinnamon), ginseng (or ginsenosides found in ginseng, and combinations thereof, for reducing the impact of blood sugar levels in the body on the human body when all are ingested.

According to another aspect of the invention, a comestible product suitable for ingestion by a human is provided comprising a combination of Products A and B packaged together, Product A being an ingestible product (other than table sugar) by the human and Product B reduces the impact of blood sugar levels in the body on the human body.

According to another aspect of the invention, the product may be such wherein Product A is an artificial sweetener and Product B comprises cinnamon or ginseng or combinations thereof, each in effective non-toxic amounts.

According to another aspect of the invention, the product may be such wherein when Product B is cinnamon, the amount of cinnamon present comprises an effective non-toxic amount to maintain or reduce blood sugar levels in the body.

According to another aspect of the invention, the product may be such wherein the effective amount of cinnamon comprises polyphenols or polyphenol polymers present in the cinnamon in the effective non-toxic amount of at least about 12% (w/w) polyphenols.

According to another aspect of the invention, the product may be such wherein when Product B is ginseng, the effective amount of ginseng present is in the form of ginseng extract standardized 1.5 to 7% of ginsenosides.

According to another aspect of the invention, the package may be such wherein the at least one ingestible ingredient comprises effective amounts of cinnamon and ginseng and the amounts may be from cinnamon extract and ginseng extract mixed with the artificial sweetener.

According to another aspect of the invention, the package wherein the cinnamon extract includes cinnamon aqueous extract TC112 which has at least about 12% (w/w) polyphenols.

According to another aspect of the invention, the package may be such wherein the ginseng extract includes ginseng extract standardized at 1.5 to 7% of ginsenosides.

According to another aspect of the invention, the package may be such wherein the ratio of cinnamon extract to ginseng extract is 1 to 1 by weight.

According to another aspect of the invention, the mix may be such wherein the at least one beneficial ingredient comprises effective non-toxic amounts of cinnamon and ginseng and the amounts may be from cinnamon extract and ginseng extract mixed with the artificial sweetener.

According to another aspect of the invention, the mix may be such wherein the cinnamon extract includes cinnamon aqueous extract TC112 which has at least one 12% (w/w) polyphenols.

According to another aspect of the invention, the mix may be such wherein the ginseng extract includes ginseng extract standardized at 1.5 to 7% of ginsenosides.

According to another aspect of the invention, the mix may be such wherein the ratio of cinnamon extract to ginseng extract is 1 to 1 by weight.

According to another aspect of the invention, the package may be such wherein the polyphenols contain at least about 1% Type A polymers.

According to another aspect of the invention, the mix may be such wherein the polyphenols contain at least about 1% Type A polymers.

DETAILED DESCRIPTION OF INVENTION

In one example embodiment, there is provided a composition comprising cinnamon extract for example TC112 and ginseng extract containing for example 1.5 to 7% ginsenosides.

In another example embodiment, there is provided a use of such a composition to improve cognitive function in diabetics.

In another example embodiment, there is provided a food product containing the composition.

In "Effects of a cinnamon extract on plasma glucose, $HbA_{1c}$, and serum lipids in diabetes mellitus type 2", *European Journal of Clinical Investigation* 36, 340-344, 2006 by B. Mang et al., it was investigated that cinnamon extract seemed to have a moderate effect in reducing fasting plasma glucose concentrations in diabetic patients with poor glycaemic control. A cinnamon capsule was used which contained 112 mg of the aqueous cinnamon extract TC112 prepared by Finzelberg (Andernach, Germany), an amount equivalent to 1 g of cinnamon, thus corresponding to 1 g of cinnamon.

The use of purified aqueous cinnamon extract for 4 months resulted in a 10.3% decrease in fasting blood sugar compared to 3.3% in the placebo group. TC112 capsules 112 mg of aqueous cinnamon extract corresponding to 1 g of cinnamon.

TABLE 2

Variables of glucose and lipid metabolism at baseline and after the intervention period

| Variable | Cinnamon group (n = 33) | Placebo group (n = 32) |
| --- | --- | --- |
| Fasting plasma glucose at baseline (mmol $L^{-1}$) | 9.26 ± 2.26 | 8.66 ± 1.47 |
| Fasting plasma glucose postintervention (mmol $L^{-1}$) | 8.15 ± 1.65† | 8.31 ± 1.62 |
| Differences‡ of fasting glucose (mmol $L^{-1}$) | 1.11 ± 1.59§ | 0.35 ± 1.29 |

Mang et al. Effects of a cinnamon extract on plasma glucose, HhA1c, serum lipids in diabetes mellitus type 2. *Eur J Clin Investig* 36: 340-344, 2006

The beneficial effects of cinnamon extract are the Polyphenols found in its water-soluble fractions. The major active component of the cinnamon extract appears to be doubly linked procyanidin type-A polymers (Anderson et al., 2004). CE has been reported to have anti-oxidant effects in rats (Lee et al., 2003; Lin et al., 2003; Anderson et al., 2004) and humans, insulin-potentiating effects in rats (Qin et al., 2003; 2004), mice (Kim et al., 2006) and humans (Khan et al., 2003; Ziegenfuss et al., 2006; Wang et al., 2007). Cinnamon extract also prevents insulin resistance induced by a high-fructose diet in rats (Qin et al., 2004). In addition, cinnamon decreases levels of glucose, triglycerides, and LDL cholesterol in people with type-2 diabetes (Khan et al., 2003).

Water-soluble polyphenol polymers are believed to be the key components responsible for its beneficial metabolic effects (Anderson et al., *J. Agric. Food Chem.* 2004, 52, 65-70); they enhance the activity of insulin and are antioxidants. The polyphenol type-A polymers from cinnamon upregulate genes involved in blood sugar control (Imparl-Radosevich et al., *Horm res* 50(3):177-182, 1998). These polymers are composed of monomeric units with a molecular mass of 288. Two trimers with a molecular mass of 864 and a tetramer with a mass of 1152. Their protonated molecular masses indicated that they are A type doubly linked procyanidin oligomers of the catechins and/or epicatechins. (*J. Agric. Food Chem.* 2004, 52, 65-70).

In "Cinnamon improves glucose and lipids of people with type 2 diabetes.", *Diabetes Care* 26:3215-3218, 2003 by A. Khan et al., a human study was conducted involving subjects with type 2 diabetes consuming cinnamon. Subjects consumed 1, 3, or 6 g of cinnamon per day for 40 days with 3 placebo groups corresponding to the three groups that consumed different numbers of capsules containing cinnamon. There were decreases in fasting serum glucose (18-29%), triglycerides (23-30%), total cholesterol (12-26%), and LDL cholesterol (7-27%) after 40 days. Benefits in insulin sensitivity were also likely to lead to decreased incidence of cardiovascular diseases, which is more than double in people with diabetes.

The following Table 1 from Khan, et al., illustrates the effects of cinnamon on glucose levels in people with type 2 diabetes

| Group* | Doses of cinnamon (g/day) | Fasting serum glucose level (mmol/l)† | | | |
|---|---|---|---|---|---|
| | | Before cinnamon intake | During cinnamon intake | | After cinnamon intake |
| | | Day 0 | Day 20 | Day 40 | Day 60 |
| 1 | 1 | $11.6 \pm 1.7^a$ | $10.5 \pm 1.8^{ab}$ | $8.7 \pm 1.6^c$ | $9.7 \pm 1.4^{bc}$ |
| 2 | 3 | $11.4 \pm 1.2^a$ | $9.9 \pm 1.1^{ab}$ | $9.4 \pm 1.1^b$ | $9.9 \pm 1.6^{ab}$ |
| 3 | 6 | $13.0 \pm 1.4^a$ | $10.2 \pm 1.3^{bc}$ | $9.2 \pm 1.5^c$ | $11.4 \pm 1.8^{ab}$ |
| 4 | Placebo 1 | $12.2 \pm 1.0^a$ | $12.7 \pm 0.8^a$ | $12.4 \pm 1.1^a$ | $12.6 \pm 1.0^a$ |
| 5 | Placebo 2 | $12.4 \pm 1.0^a$ | $11.8 \pm 0.9^a$ | $12.7 \pm 1.0^a$ | $12.6 \pm 1.3^a$ |
| 6 | Placebo 3 | $16.7 \pm 1.4^a$ | $16.7 \pm 1.6^a$ | $16.8 \pm 1.7^a$ | $17.0 \pm 1.3^a$ |

Data are means ± SD.
*Ten individuals in each group;
†means followed by different superscript letters in the same row are significantly different at $P < 0.05$.

In "Isolation and Characterization of Polyphenol Type-A Polymers from Cinnamon with Insulin-like Biological Activity", *J agric food chem.* 52(1):65-70, 2004 by Anderson et al., it was investigated that water-soluble polyphenol polymers from cinnamon would increase insulin-dependent in vitro glucose metabolism roughly 20-fold and display antioxidant activity. Certain studies demonstrated that water-soluble polymeric compounds isolated from cinnamon have insulin-enhancing biological activity in the in vitro assay measuring the insulin dependent effects on glucose metabolism and also function as antioxidants. These same compounds have been shown to inhibit phosphotyrosine phosphatase in the insulin-receptor domain and to activate insulin receptor kinase and function as a mimetic for insulin in 3T3-L1 adipocytes.

There are two types of cinnamon: Ceylon and cassia, both derived from the bark of evergreen trees. Ceylon cinnamon is grown in South America, Southeast Asia, and the West Indies, while cassia cinnamon is grown in Central America, China, and Indonesia. Ceylon cinnamon bark looks like tightly rolled scrolls, while cassia cinnamon is more loosely rolled. Cassia is the variety most commonly sold in the United States.

Several polyphenolic polymer compounds have been isolated from cinnamon bark. In test tube assays using fat cells, the polyphenolic polymers were found to increase sugar metabolism a whopping 20-fold. Previous studies suggest that compounds from cinnamon exhibit insulin-like activity in cells, intact animals and people with type 2 diabetes.

To understand the molecular basis of the insulin-like activity and explore additional benefits of cinnamon, the effects of compounds from cinnamon were investigated on the utilization of sugar and control of insulin function. The results showed that factors from cinnamon improve/inhibit factors involved in inflammation. These results suggest that compounds from cinnamon were involved in the use of sugar by cells.

It has also been shown that cinnamon improves glucose and lipid profiles of people with type 2 diabetes and that a water-soluble cinnamon extract and HPLC-purified cinnamon polyphenols (CP) display insulin-like activity. The objective of the study was to investigate the biochemical basis for the insulin-like effects of cinnamon. Immunoblotting procedure was employed to analyze three proteins, insulin receptor (IR), glucose transporter 4 (GLUT4), and the anti-inflammatory protein tristetraprolin (TTP) involved in insulin signal transduction pathway in mouse 3T3-L1 adipocytes. The results showed that both insulin and CP increased the levels of the three proteins, and recombinant TTP was phosphorylated in vitro by glycogen synthase kinase 3 beta and protein kinases A, B, and C. These results suggest that like insulin, CP increase the amount of the three critically important proteins involved in insulin signaling, glucose transport and inflammatory response. A model of actions was proposed to link CP and TTP in insulin signal transduction pathway. The study provided new biochemical evidence for the beneficial effects of CP in insulin-like action and suggests anti-inflammatory properties of CP.

Preferably the type of cinnamon extract to be used should contain at least 12% (w/w) of water-soluble polyphenol polymers without volatile oils. The polyphenol polymers should preferably be Type-A polymers doubly linked procyanidin oligomers of the catechins and/or epicatechins.

Cinnamon extract can be used in doses ranging between about 50 to about 1,000 mg/day.

Cinnamon extract in the amounts of 50 to 1,000 mg/day which contain 12% of polyphenols are approximately equivalent to 0.5 to 6 grams per day of Cinnamon powder. These polyphenol polymers are composed of monomeric units with a molecular mass of 288, two trimers with a molecular mass of 864 and a tetramer with a mass of 1152.

The major active component of cinnamon extract, it is believed, appears to be the doubly linked procyanidin Type-A polymers.

The total phenolic content of cinnamon extract and its antioxidant potential are both predictive of the extract's ability to inhibit protein glycation (Dearlove et al., *J of Medicinal Food* 11 (2):275-281. 2008). Glucose and fructose form glycation products linked to serious diseases. For example, postprandial fructose has been linked to retinopathy in diabetics (Kawsaki et al., *Metabolism* 53: 583-588, 2004) and fructose has been implicated in symptoms of metabolic syndrome (Kawasaki et al., *Diabetes Care* 25:353-357, 2002).

Reference should also be had to Hlebowicz et al., *Effect of cinnamon on postprandial blood glucose, gastric emptying, and satiety in healthy subjects. Am J Clin Nutr* 85:1552-6, 2007 which teaches the following:

Cinnamon (6 g) reduced postprandial blood glucose AUC by 52% at 45 minutes (from 68.1 to 32.4, table 1) in healthy people.

TABLE 1

Postprandial blood glucose areas under the curve (AUCs) in healthy subjects after ingestion of meals consisting of rice pudding with or without added cinnamon[1]

| AUC | Rice pudding without Cinnamon | Rice pudding with cinnamon |
|---|---|---|
| | mmol * min/L | |
| 0-15 min | $6.8 \pm 1.8$ | $3.6 \pm 1.0$ |
| 0-30 min | $30.7 \pm 5.1$ | $13.7 \pm 3.4^2$ |

TABLE 1-continued

Postprandial blood glucose areas under the curve (AUCs) in healthy subjects after ingestion of meals consisting of rice pudding with or without added cinnamon[1]

| AUC | Rice pudding without Cinnamon | Rice pudding with cinnamon |
|---|---|---|
| | mmol * min/L | |
| 0-45 min | 68.1 ± 8.2 | 32.4 ± 6.6[2] |
| 0-60 min | 97.2 ± 11.0 | 47.3 ± 9.2[2] |
| 0-90 min | 125.0 ± 16.8 | 63.3 ± 11.7[2] |
| 0-120 min | 139.1 ± 19.6 | 75.0 ± 13.7[2] |

[1]All values are x ± SEM; n = 14. Significant differences in postprandial blood glucose AUCs were evaluated with Wilcoxon's t test.
[2]Significantly different from rice pudding without cinnamon, P < 0.05.

Ginseng also reduces plasma glucose concentration in the human. The effective amount of ginseng preferably present, is in the form of ginseng extract standardized at 1.5 to 7% of ginsenosides.

The term ginseng refers to several species of the genus *Panax*. For more than two thousand years, the roots of this slow-growing plant have been valued in Chinese medicine. The two most commonly used species are Asian ginseng (*Panax ginseng* C. A. Meyer), which is mostly extinct in its natural range but is still cultivated, and American ginseng (*P. quinquefolius* L.), which is both harvested from the wild and cultivated. *Panax ginseng* should not be confused with Siberian ginseng (*Eleutherococcus senticosus*). In Russia, Siberian ginseng was promoted as a cheaper alternative to ginseng and was believed to have identical benefits. However, Siberian ginseng does not contain the ginsenosides that are present in the *Panax* species, which are believed to be active ingredients and have been studied scientifically.

In "Ginsengs: A Review of Safety and Efficacy", *Nutrition in Clinical Care* 3(2):90, 2000 by Gail E. Mahady et al., an investigation of ginseng involved a standardized extract of *panax ginseng* containing 1.5 to 7% of ginsenosides. The recommended dose was 0.5 to 2 g per day of dried root, corresponding to 100 to 300 mg per day of this extract.

In another example, in Ginsana G2G® (a ginseng supplement) the recommended daily dose is 200 mg of ginseng extract per day.

According to the U.S. National Institutes of Health website, the daily therapeutic dosage of ginseng root is 0.5-2 g of the dried root, or 100 to 300 mg per day of a standardized extract containing 1.5 to 7% ginsenosides, or other preparations taken correspondingly.

The German Commission E recommends *Panax ginseng* at the dosage of 1-2 g of root or equivalent preparations taken daily.

Standardized extracts are recommended with the dosage of 200-500 mg daily. Capsules of powdered root extracts are recommended with the dosage of 200-500 mg daily or 1-4 g of powdered root per day.

Tincture is recommended at the dosage of 1-2 ml daily of 1:1 extract (equivalent to 1-2 grams ginseng root).

Positive clinical trials with *Panax ginseng* generally involve a dosage of greater than 1 gram per day.

According to the U.S. National Institutes of Health, exceeding the recommended dose of Asian ginseng may cause adverse reactions such as hypertension, diarrhea, nervousness and insomnia. They also note that while there are no contraindications, *Panax ginseng* should be used with caution during pregnancy, nursing, and in children under the age of 12 years old, as safety data is currently unavailable.

Ginsenosides are a group of triterpenoid saponins that can be classified into two groups by the skeleton of their aglycones, namely dammarane- and oleanane-type. Ginsenosides are found nearly exclusively in *Panax* species (ginseng) and up to now more than 150 naturally occurring ginsenosides have been isolated from roots, leaves/stems, fruits, and/or flower heads of ginseng. Ginsenosides have been the target of a lot of research as they are believed to be the main active principles behind the claims of ginseng's efficacy. The potential health effects of ginsenosides include antidiabetic effects. Ginsenosides can be metabolized in the stomach (acid hydrolysis) and in the gastrointestinal tract (bacterial hydrolysis) or transformed to other ginsenosides by drying.

Thus, the cinnamon extract may include cinnamon aqueous extract TC112 which has at least about 12% (w/w) polyphenols (preferably containing at least about 1% doubly-linked polyphenol Type A polymers). The ginseng extract may include ginseng extract from *panax ginseng* standardized at 1.5 to 7% of ginsenosides. In one embodiment, the ratio of cinnamon extract to ginseng extract is 1 to 1 by weight.

With respect to daily dosages of the cinnamon extract which is 120 mg of cinnamon aqueous extract having at least about 12% (w/w) polyphenols and the ginseng extract is equivalent of 120 mg of ginseng standardized at 1.5 to 7% of ginsenosides.

A composition is described herein which includes cinnamon extract and ginseng extract admixed in a single compound. The cinnamon extract includes cinnamon aqueous extract TC112. The ginseng extract includes ginseng extract includes *panax ginseng* extract standardized at 1.5 to 7% of ginsenosides.

In one embodiment, the ratio of cinnamon extract to ginseng extract is 1 to 1 by weight. The composition is embodied in the form of a daily dosage (such as a pill or food product) wherein the cinnamon extract is 120 mg of cinnamon aqueous extract and the ginseng extract is 120 mg of ginseng standardized at 1.5 to 7% of ginsenosides.

The composition may be used in additional example applications.

The composition is expected to for example provide a synergistic combination to be used for the improvement of cognitive function, the prophelactic treatment and prevention of Alzheimer's disease or arterial complications, the maintenance or lowering of blood-sugar levels, for consumption by diabetics, or any combination thereof.

In another example, the composition is expected to be used in the form of a daily dosage to assist in memory and cognitive functions that are often experienced a sustained or partial memory impairment or memory dysfunction that is due to either Type 1 or Type 2 diabetes or from a pre-diabetic state or from any form of memory impairment due to other conditions such as stroke, head injury, excessive intoxication and when administered in any form as so described.

In another example, the composition may be used for lowering of blood glucose levels by stimulating insulin release. The composition is expected to impart a combined synergistic effect to help improve cognitive function to those affected by high glucose levels in the body. For example, the composition may be used to prevent Alzheimer's disease such as, for example, in diabetics.

In another example, the composition is expected to therefore help to reduce instances of arterial disease (such as coronary arterial disease) to diabetics, who may be particularly prone to such diseases, by controlling sugar levels.

In one example, the composition may be compounded into a multi-vitamin, vitamin supplement or combined in an effervescent capsule or tablet that releases the composition into hot or cold water. This may for example be used when afflicted with the common cold, flu or other congestive respiratory disorders or may be mixed with cough suppressants, cough syrups, cough gels, wafer, instantly soluble wafers, cough drops or other sprays, whether oral or nasal and so combined with such ingredients.

In another example, the composition may be compounded, formulated, made into tablets, gels, gel capsules, or combined with water, flavors, additives, thickeners, chocolate products, cocoa, sugar, high fructose corn syrup, oils, fragrances, meats, or meat by-products, vegetables or vegetable by-products, chemical derivatives of natural compounds or compound extracts including but not limited to agar, carrageen, starch, and subsequent products maybe cooked, baked, roasted, toasted, flamed, dried or preserved in any commercial or consumer appliances or otherwise derivative components made thereof and represented to improve, augment, sustain, enhance or otherwise change the levels of blood glucose while improving memory in conjunction with the lowering of blood sugars, particularly for the use by persons or animals suffering from diabetes or diabetic type disorders that are not limited to type 1 or type 2 diabetes but may also include disorders that are associated with diabetes or the pre-diabetic state that may or may not affect memory and cognition.

The composition may also be provided in a food product.

In one example, the composition is contained in a ready-to-eat food that is high in dietary fiber, low in sugars and contains protein and other vitamins and supplements such as Thiamin B1, Riboflavin, calcium, and Niacin.

In another example, a food product is provided containing the composition and is prepared with a dairy food product such as a ½ cup of 2% low fat milk, cornstarch, cocoa processed with alkali, modified food starch, salt and contains less than 2% of natural flavor, artificial flavor, calcium carrageenan (thickener), fumaric acid (for thickening), aspartame (or other artificial sweetener), hydrogenated soy bean oil, polysorbate 60 (prevents scorching), and colorants acceptable to foods and food regulations as well as a preservative such as BHA. The food product may for example be prepared by mixing all of the ingredients and heating to a full-boil over medium heat, then pouring into cups and cooling. Pre-made mixtures may also be made and stored and sold in cold lockers to the consumer.

In another example, a prepared hot or cold drink is provided using ingredients such as vanilla or cocoa, cornstarch or other similar starches and natural flavors as well as artificial flavors in combination with milk to make a chocolate or vanilla milk drink that maybe enjoyed hot or cold and that includes the composition. Such combinations may also be combined with coffee, tea or other stimulant drinks and served either hot or cold or stored for purchase by the consumer using ready-to-drink formulae.

In another example, a ready-to-eat chocolate bar or chocolate combination snack is provided with the composition, providing a lower calorie, low-sugar chocolate alternative.

In another example, the composition may generally be added as a component of the flavoring and enhancement of ready-to-eat food as well as ready-to-drink products in a dispensing packaging similar to those containing conventional herbs and spices. The composition may for example be used in the kitchen when combined with other spices, herbs, flavorings, thickeners and other customary combinations for the preparation of foods that are ready-to-eat or ready-to-drink.

In another example, an encapsulated product is provided containing the composition. The encapsulated product is protective to the consumer's palate and does not impart a bitter or off-flavor taste. The encapsulation method uses commercially available coatings that are approved for human and animal use. Encapsulating agents maybe but not limited to; sugar free compounds, starch or starch derivatives, liposome's or liposome derivatives, nano-particles or larger and the use of nano-forming particles or particulates in the nano molecular size or larger. Encapsulated materials may be air dried, freeze dried or desiccated by any commercial means and said powders or dried materials or partially dried materials may be combined with other flavors, fragrances and other stabilizing agents to form a concentrate and used in the making or manufacturing of food ready-to-eat or ready-to-drink consumer products or may be used in the preparation of foods or snacks for either human or animal consumption.

In another example, the composition may for example be added or compounded into the following food products (without intending to be limiting): bread, bread products, bread substitutes, bran, and bran containing products, high fiber products, low fiber products, yogurt or yogurt like products, cheese or cheeses made from the milk of animals or artificial cheeses made from other products and resemble the consistency and texture of cheese, ice cream, soft drinks, water augmented drinks, fruit and vegetable drinks, condiments and candies, dried fruits and nuts and other dried product combinations, meat and meat by-products, prepared or frozen or frozen prepared vegetables and fruits, pies, cakes or mixtures of such, muffins, cookies or other snacks such as chips made from any product, seasonings and seasonings added to products or used in salads, vegetables, fruits or prepared dishes.

In another example, the cinnamon and ginseng elements of the composition are maintained separately and are combined prior to consumption or processing within a food product.

It can be appreciated that other forms of cinnamon extract and ginseng extract may be used other than those specifically described herein. Particularly the active components—polyphenols from cinnamon and ginsenosides from ginseng may be combined as previously discussed.

There are no concerns of overdoses with cinnamon given in moderation. The same is expected with respect to ginseng which is relatively safe even in relatively large amounts.

Where ginseng extract is used instead of raw ginseng, the extract would have for example a ginsenoside content at least equivalent to or slightly greater than the ginsenoside content of the raw ginseng used. This is because ginseng extract is more concentrated than raw ginseng. Thus ginseng extracts used would have equivalent ginsenoside content as for example between about 0.14 grams of raw ginseng to about 0.6 grams of raw ginseng.

These amounts of cinnamon and ginseng can be adjusted up or down as desired. As may be the equivalent amount of extract of each or the amount of polyphenols or ginsenosides.

A Certificate of Analysis for Batch No. CC/08007 from Natural Remedies Private Limited yielded the following test results in respect of suitable *cinnamomum cassia* extract suitable for use herein.

>12% total polyphenols

Botanical Name *Cinnamomum cassia*

| | |
|---|---|
| Part used | bark |
| Extract ratio | 20:1 |
| Solvent used | Water, Methanol |
| Excipients | Collodal silicon dioxide (0-2% approx.) |

| SL. NO. | TESTS | SPECIFICATION | RESULT | TEST PROTOCOL |
|---|---|---|---|---|
| 1. | Description | Reddish brown to Dark brown powder | Brown powder | — |
| 2. | HPLC Fingerprint | To pass the test | Compiles | By HPLC [NR/QCD/APM04 WI(49)] |
| 3. | Moisture (% w/w) | <8.0 | 4.3 | As per USP <921> Method II |
| 4. | pH (5% w/v solution) | 4.0-7.0 | 5.1 | As per USP <791> |
| 5. | Total ash content (% w/w) | <15.0 | 6.4 | As per USP <561> |
| 6. | Acid insoluble Ash (% w/w) | <5.0 | 0.2 | As per USP <561> |
| 7. | Bulk density (g/cc) | 0.15-0.60 | 0.42 | As per USP <616> Method -I |
| 8. | Tapped bolk density (g/cc) | 0.20-0.80 | 0.64 | |
| 9. | Total soluble solids (% w/w) | >90.0 | 90.8 | As per USP <561> |
| 10. | Material passing through 30# BS/35 ASTM (% w/w) | >99.0 | 100 | As per USP <786> Particle size distribution |
| 11. | Heavy Metals | | | AAS/ICP-ES |
| | Lead | <5.0 ppm | <0.1 | |
| | Arsenic | <2.0 ppm | <0.1 | |
| | Cadmium | <0.2 ppm | <0.1 | |
| | Mercury | <0.1 ppm | <0.1 | |
| 12. | Microbiology Test | | | As per WHO/PHARM/92.559/ Rev. 1, Pg. 49 |
| | Total viable aerobic count | <$10^3$ cfu $g^{-1}$ | 200 | |
| | Total fungal count | <$10^3$ fs $g^{-1}$ | No growth | |
| | Total *enterbacter iaceae* | <$10^3$ org $g^{-1}$ | <100 | |
| | *E. coli* | Absent | Complies | |
| | *Salmonella* species | Absent | Complies | |
| | *S. aureus* | Absent | Complies | |
| 13. | Courmarin content (ppm) | <100.0 | Complies | By HPLC |
| 14. | Bio-assay α-amylase Inhibition $IC_{50}$ (mcg/ml) | <100.0 | Complies | [NR/BSY/SOP/004/01] |
| 15. | Phytochemical Analysis Total polyphenols (% w/w) | ≥12.0 | 12.5 | By Spectrophotometry [NR/QCD/APM06 WI(18)] |

A Certificate of Analysis for Ginseng Dry Extract 108, Analysis Certificate N. 68297/1 in respect of *Panax ginseng* C. A. Meyer suitable for use herein gave the following test results in respect of the extract.

| Determination | Results | Specification | U.M. |
|---|---|---|---|
| Extract/Drug ratio | 1:4 | 1:3-5 | |
| HPLC Contents Of total ginsenosides and malonyl ginsenosides, with reference to the dried substance | 11.8 | ≥7.0 | % |
| Ginsenoside Rg1 With reference to the dried substance | 0.99 | 0.9-1.4 | % |
| Ginsenoside Rb1 With reference to the dried substance | 1.94 | 1.7-3.0 | % |
| Ratio Number Rg1/Rb1 | 51.0 | ≥45.0 | % |
| Characters Brown-yellow amorphous powder | Complies | Complies | % |
| HPLC Identification | Complies | Complies | |
| pH (c = 5, ethanol (30% v/v)) | 5.6 | 4.0-6.0 | |
| Loss on Drying (T = 105° C., in vacumm, t = 3 h) | 3.5 | ≤7.0 | % |
| Residue on Ignition USP | 5.5 | ≤9.0 | % |
| Lead | <0.8 | ≤5.0 | ppm |
| Cadmium | <0.1 | ≤0.2 | ppm |
| Mercury | <0.05 | ≤0.1 | ppm |
| Total residual Organic Solvents | 0.14 | ≤0.5 | % |
| Ethanol | 0.14 | ≤0.25 | % |
| Hexane | <3.0 | ≤50.0 | ppm |
| Sum of other solvents | <11.0 | ≤50.0 | ppm |
| Microbiological Control According to USP | | | |
| Bacteria TM/0251 | <3000.0 | ≤3000.0 | cfu/g |
| Molds and Yeasts TM/0252 | <100.0 | ≤100.0 | cfu/g |
| *Escherichia Coli* TM/0253 | Absent | Absent | /g |
| *Salmonella* TM/0254 | Absent | Absent | /10 g |
| *Staphylococcus Aureus* TM/0255 | Absent | Absent | /g |
| *Pseudomonas Aeruginosa* TM/0256 | Absent | Absent | /g |
| Pesticide Determination Acc. To specification Eur. Ph. Methods P-PRO-15 and P-PRO-16 Pesticide Determination Method P-FA-253 | Complies | Complies | |
| Pesticide of Pentachlorobenzene | <0.01 | ≤0.01 | ppm |
| Pesticide of Technazene | <0.01 | ≤0.01 | ppm |
| Pesticide of 2,3,5,6-Tetrachloroaniline | <0.01 | ≤0.01 | ppm |
| Pesticide of Hexachlorobenzene | <0.01 | ≤0.01 | ppm |
| Pesticide of α-Hexachlorocyclohexane | <0.01 | ≤0.01 | ppm |
| Pesticide of Pentachlorocyclobenzene | <0.01 | ≤0.01 | ppm |
| Pesticide of γ-Hexachlorocyclohexane | <0.01 | ≤0.01 | ppm |
| Pesticide of β-Hexachlorocyclohexane | <0.01 | ≤0.01 | ppm |
| Pesticide of Pentachloroaniline | <0.01 | ≤0.01 | ppm |
| Pesticide of δ-Hexachlorocyclohexane | <0.01 | ≤0.01 | ppm |

-continued

| Determination | Results | Specification | U.M. |
|---|---|---|---|
| Pesticide of Pentachlorothioanisole Aflatoxin Determination According to method P-PRO-20 | <0.01 | ≤0.01 | ppm |
| Aflatoxins as a sum of B1, B2, G1 and G2 | <0.7 | ≤4.0 | ppb |
| Aflatoxin B1 | <0.1 | ≤2.0 | ppb |

While example embodiments have been described in detail in the foregoing specification, it will be understood by those skilled in the art that variations may be made without departing from the scope of the application.

The invention claimed is:

1. A composition suitable for use for ingestion in a human for enhancing the effect of the individual ingredients, the composition consisting essentially of:
 a first ingredient selected from cinnamon extract containing at least about 12% w/w polyphenols without volatile oil;
 a second ingredient selected from ginseng extract standardized at 1.5 to 7% ginosenosides; and
 optionally a suitable carrier; wherein the first ingredient is in an amount between 50 mg to 1000 mg and the second ingredient is in an amount between 200 mg to 500 mg, and wherein said composition has minimal heavy metals, residual organic solvents, and aerobic bacterial and fungal counts.

2. The composition of claim 1 wherein the ratio of the first ingredient to the second ingredient is 1:1 by weight.

3. The composition of claim 2 wherein the weight of the ginseng extract is between 100 to 300 mg.

4. The composition of claim 2 wherein the weight of the ginseng extract is between 200 mg-500 mg.

5. The composition of claim 2 wherein the composition is in the form of a daily dosage, and wherein the first ingredient comprises cinnamon aqueous extract in an amount of 120 mg, and the second ingredient is in an amount of 120.

6. The composition of claim 1 or 2, wherein the composition is in the form of a dosage for the improvement of cognitive function.

7. The composition of claim 1 or 2, wherein the composition is in the form of a dosage for the treatment of Alzheimer's disease in diabetics.

8. The composition of claim 1 or 2, wherein the composition is in the form of a dosage for the maintenance or lowering of blood-sugar levels.

9. The composition of claim 1 or 2, wherein the composition is in the form of a dosage for the treatment of arterial disease in diabetics.

10. The composition of claim 1 or 2, wherein the composition is in the form of a dosage for the improvement of cognitive function and the maintenance or lowering of blood-sugar levels.

11. The composition of claim 1 or 2, wherein the composition is in the form of a dosage for the improvement of cognitive function in diabetics.

12. The composition of claim 2 wherein the amount of the ginseng extract is 100 mg.

13. The composition of claim 2 wherein the amount of the ginseng extract is 300 mg.

14. The composition of claim 2 wherein the amount of the ginseng extract is 200 mg.

15. The composition of claim 2 wherein the amount of the ginseng extract is 500 mg.

16. The composition of claim 12, 13, 14 or 15 in the form of a dosage for the improvement of cognitive function.

17. The composition of claim 12, 13, 14 or 15, wherein the composition is in the form of a dosage for the treatment of Alzheimer's disease in diabetics.

18. The composition of claim 12, 13, 14 or 15, wherein the composition is in the form of a dosage for the maintenance or lowering of blood-sugar levels.

19. The composition of claim 12, 13, 14 or 15, wherein the composition is in the form of a dosage for the prevention of arterial disease in diabetics.

20. The composition of claim 12, 13, 14 or 15, wherein the composition is in the form of a dosage for the improvement of cognitive function and the maintenance or lowering of blood-sugar levels.

* * * * *